United States Patent
Barak et al.

(10) Patent No.: US 9,651,498 B2
(45) Date of Patent: May 16, 2017

(54) OPTICAL METHOD AND SYSTEM FOR DETECTING DEFECTS IN THREE-DIMENSIONAL STRUCTURES

(71) Applicant: NOVA MEASURING INSTRUMENTS LTD., Rehovot (IL)

(72) Inventors: Gilad Barak, Rehovot (IL); Elad Dotan, Talmei Yehiel (IL); Alon Belleli, Gedera (IL)

(73) Assignee: NOVA MEASURING INSTRUMENTS LTD., Rehovot (IL)

( * ) Notice: Subject to any disclaimer, the term of this patent is extended or adjusted under 35 U.S.C. 154(b) by 176 days.

(21) Appl. No.: 14/412,479

(22) PCT Filed: Jul. 2, 2013

(86) PCT No.: PCT/IL2013/050560
§ 371 (c)(1),
(2) Date: Jan. 2, 2015

(87) PCT Pub. No.: WO2014/006614
PCT Pub. Date: Jan. 9, 2014

(65) Prior Publication Data
US 2015/0192527 A1    Jul. 9, 2015

Related U.S. Application Data

(60) Provisional application No. 61/666,935, filed on Jul. 2, 2012.

(51) Int. Cl.
G01N 21/00 (2006.01)
G01N 21/88 (2006.01)
(Continued)

(52) U.S. Cl.
CPC ......... G01N 21/8806 (2013.01); G01N 21/55 (2013.01); G01N 21/9501 (2013.01);
(Continued)

(58) Field of Classification Search
CPC ............... G01N 21/8806; G01N 21/55; G01N 21/9501; G01N 2021/8825; G01N 2201/12; G01J 22/12
(Continued)

(56) References Cited

U.S. PATENT DOCUMENTS 6,991,514 B1    1/2006  Meloni et al.
2002/0107650 A1 *    8/2002  Wack ................. G01N 21/211
                                                          702/81
(Continued)

FOREIGN PATENT DOCUMENTS

WO    2012/098550    7/2012

*Primary Examiner* — Hina F Ayub
(74) *Attorney, Agent, or Firm* — Browdy and Neimark, PLLC

(57) ABSTRACT

A method and system are presented for use in inspection of via containing structures. According to this technique, measured data indicative of a spectral response of a via-containing region of a structure under measurements is processed, and, upon identifying a change in at least one parameter of the spectral response with respect to a spectral signature of the via-containing region, output data is generated indicative of a possible defect at an inner surface of the via.

18 Claims, 3 Drawing Sheets

(51) Int. Cl.
　　　*G01N 21/95*　　　(2006.01)
　　　*H01L 21/66*　　　(2006.01)
　　　*G01N 21/55*　　　(2014.01)
(52) U.S. Cl.
　　　CPC ...... *H01L 22/12* (2013.01); *G01N 2021/8825* (2013.01); *G01N 2201/12* (2013.01)
(58) Field of Classification Search
　　　USPC ...................................................... 356/237.6
　　　See application file for complete search history.

(56)　　　　　　　References Cited

U.S. PATENT DOCUMENTS

| | | | |
|---|---|---|---|
| 2004/0235205 A1* | 11/2004 | Levy .................... | G01N 21/211 438/14 |
| 2006/0038980 A1* | 2/2006 | Naka ...................... | G01N 21/65 356/73 |
| 2010/0284027 A1 | 11/2010 | Scheiner | |
| 2011/0228263 A1* | 9/2011 | Chuang .............. | G01N 21/9501 356/300 |
| 2012/0197592 A1* | 8/2012 | Ku ........................ | G01B 11/22 702/166 |

* cited by examiner (GENERAL ART)

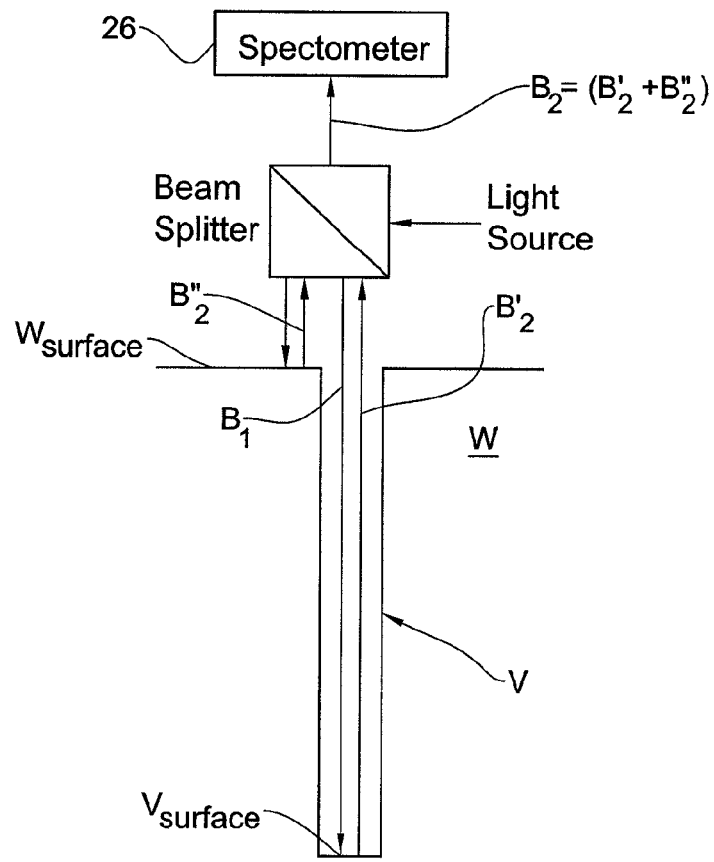
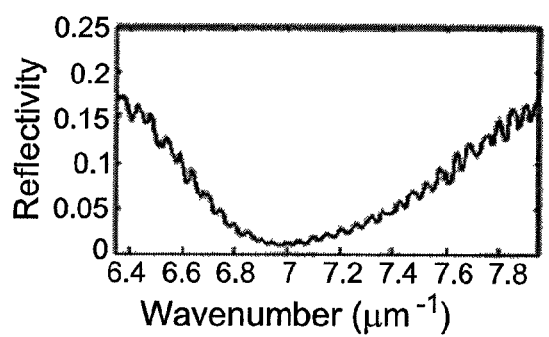
Fig. 4A
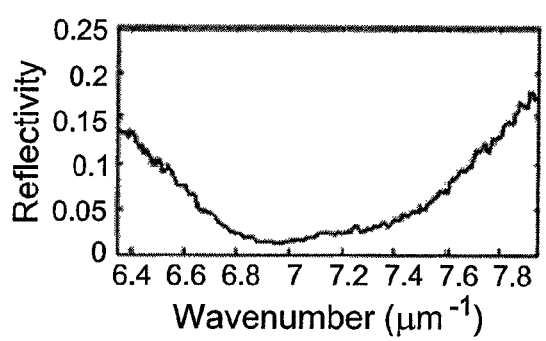
Fig. 4B

ND SYSTEM FOR
DETECTING DEFECTS IN
THREE-DIMENSIONAL STRUCTURES

TECHNOLOGICAL FIELD

The present invention is generally in the field of optical inspection/measurement techniques, and relates to an optical method and system for detecting defects in three-dimensional structures, such as semiconductor wafers.

BACKGROUND

As semiconductor technology progresses, shrinking device dimensions has become an increasingly complex task. It is known to overcome these difficulties by using vertical integration of multiple semiconductor devices (chips), allowing either larger number of devices per unit (e.g. in memory applications) or integration of chips of different functionality, thus allowing better performance of a hybrid system (e.g. sensor, processor and memory). A technique known as Through Silicon Via (TSV) has been developed for use in vertical integration of multiple semiconductor devices. TSV is a high performance technique to create 3D packages and 3D integrated circuits (as compared to its alternatives such as package-on-package), because the density of vias is substantially higher and the length of the connections is shorter. According to TSV, conducting pillars are formed within a silicon substrate, later to be used for contacting successive chips. TSV technology provides the electrical interconnect between the components in different layers, and also provides mechanical support. In TSV technology, a via is fabricated in a silicon chip with different active integrated circuit devices or other devices fabricated by a semiconductor process, and the via is filled with metal such as Cu, Au, W, solders, or a highly-doped semiconductor material such as polysilicon. Multiple components provided with such vias are then stacked and bonded together.

A critical step in the TSV process is that of via formation, in which a pattern of contacts is etched into the silicon. In order to maintain the required via quality, it is important to control both the depth and profile of the vias.

WO 2012/098550, assigned to the assignee of the present application, discloses an optical system for use in measuring in patterned structures having vias. The system is configured and operable to enable measurement of a via profile parameters. The system comprises an illumination channel for propagating illuminated light onto the structure being measured, a detection channel for collecting light returned from the illuminated structure to a detection unit, and a modulating assembly configured and operable for implementing a dark-field detection mode by carrying out at least one of the following: affecting at least one parameter of light propagating along at least one of the illumination and detection channels, and affecting propagation of light along at least the detection channel.

GENERAL DESCRIPTION

There is a need in the art for a novel technique for monitoring a TSV process. This is associated with the fact that in this process defects in a via might be produced, and accordingly in order to maintain the required via quality, it is essential to detect a defective via. The present invention provides a novel method and system for detection of via defects, based on optical reflectometry. It should be noted that, although the description below refers specifically to TSVs, the principles of the invention can be used for defect detection in grooves/vias created by any technology other than etching a silicon layer. The vias that can be inspected for defects by the technique of the invention are high aspect ratio vias, namely deep and narrow vias, TSVs being a specific but not limiting example of such type of vias.

TSVs are created by deep silicon etch, yielding a vertical hole in the silicon with high aspect ratio. Typical cross section sizes of the via (via diameters) are in the range of 1-50 µm, and depths are up to 200 µm, providing aspect ratios up to 20:1. It is important to detect any defect in a via, because defects might cause faulty coverage and/or filling of the TSV in later fabrication steps (lead to improper coating and deposition processes in the next fabrication steps), as well as might cause electrical shorts between the TSV (filled with Cu) and the Si substrate, eventually rendering the entire device unusable. Detection of such defects is of detrimental importance for the future functionality of a chip, and thus of significant industrial interest.

An example of a defect type to be timely detected is associated with the formation of sharp spikes at the via bottom. In this connection, reference is made to FIG. 1 schematically illustrating a TSV cross section, with a bottom defect.

One possible approach of characterizing such vias (i.e. grooves having high aspect ratio geometry) is through spectral-reflectometry. In this technique, broadband light is focused on a via-containing region of a wafer (generally, a patterned structure) from the top, and reflected from both the inner surfaces of the via (mainly from the via bottom) and the wafer top surface. The wavelength-dependent reflection is determined by interference properties of light reflected from the different parts of the illuminated region on the wafer.

The interference between broadband light reflected from the via surface and the wafer top surface can be expressed as spectral signature of a via-containing region for a given depth via. Such spectral signature of the illuminated via-containing region is characterized by one or more parameters, such as oscillations, e.g. fast oscillations, and may for example be described by the following expression:

$$A(k) \approx A_0(k) + A_1(k)\cos(2Dk) \qquad (1),$$

wherein A is the reflected spectrum, $k=2\pi/\lambda$ is the light wavenumber, $A_0$ and $A_1$ are slow-varying functions of k, primarily determined by the reflection intensity from the wafer top and via bottom interfaces and D is the via depth.

The second term $A_1(k)\cos(2Dk)$ in equation (1) is the oscillatory term, which is a direct result of the interference between light portions reflected from the wafer top surface and the inner surface of the via, e.g. via bottom. The spectral oscillations have a specific periodicity in k, given by 2D.

According to some embodiments of the invention, these oscillations are used as a straightforward measure of the quality of the via surface. In order for significant signal to be reflected from the via surface, so as to give rise to the spectral oscillations, the inner surface of the via, specifically its bottom surface, is to be smooth and clear from defects.

Generally, any defect in the via (e.g. bottom region) significantly alters the wavelength-dependent reflection (spectral response) of the via-containing region of a patterned structure, i.e. causes a detectable change in at least one parameter of the spectral response as compared to the spectral signature of the non-defected via-containing region, e.g. causes severe degradation of the oscillations visibility. This can be identified in the measured reflectometry signal. For example, strong fast oscillations of the signal correspond to interference component from the via surface and the wafer top surface, while a reflectometry signal from a via with a defect therein is missing these oscillations, or at least their visibility is drastically impaired.

One way of quantifying the visibility of such oscillations is through spectral analysis of the measurement. Such analysis provides a quantitative measure for the existence of typical frequencies in the data. A very common tool for such analysis is the Fourier transform, where oscillations give rise to a distinct sharp peak at the Fourier spectrogram. The position of this peak is determined by the oscillations frequency, which (as stated) is determined by the TSV depth. The method of quantifying the visibility of the fast oscillations using a Fourier transform is, of course, only one of many possible methods of spectral analysis. Other methods, such as the Pisarenko and MUSIC algorithms for harmonic decomposition, the Welch, Yule-Walker and Burg algorithms, the eigenvector spectral decomposition and many more. One can use any such method to identify and quantify the existence of a fast frequency in the measured signal, corresponding to a value consistent with the via depth. Of course, only a very rough estimate of the via depth is required in order to identify the reasonable range at which such frequency is expected.

The proposed approach can be implemented either for an isolated structure or a lattice of similar elements.

Thus, according to one broad aspect of the invention, there is provided a method for use in inspection of via containing structures. The method comprises:

receiving measured data indicative of a spectral response of a measured via-containing region;

processing and analyzing said spectral response data and upon identifying a change in at least one parameter of the spectral response with respect to a spectral signature of the via-containing region generating output data indicative of a possible defect at an inner surface of the via in said region.

According to another aspect of the invention, there is provided a system for use in inspection of via containing structures, the system comprising a control system which comprises: data input utility for receiving measured data indicative of a spectral response of a measured via-containing region; and processing and analyzing utility for processing the spectral response data, and upon identifying a change in at least one parameter of the spectral response with respect to a spectral signature of the via-containing region generating output data indicative of a possible defect in the via in said region.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 3 schematically illustrates the light propagation scheme in a reflectometry system measuring on a via-containing region of a structure;

FIGS. 4A and 4B graphically show an example of measured reflectometry spectrum for a TSV without a defect (FIG. 4A) and with a defect in the via (FIG. 4B)

DETAILED DESCRIPTION OF EMBODIMENTS

Figure 1:
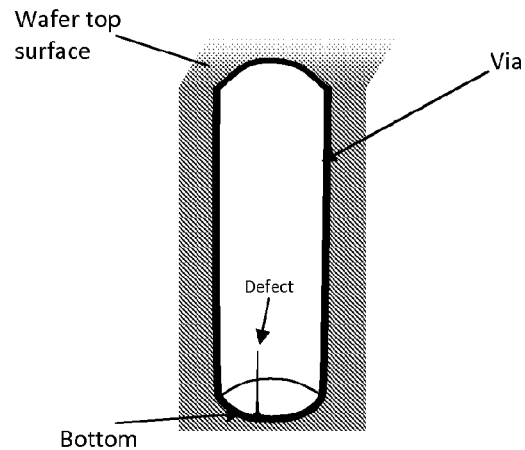
FIG. 1 schematically illustrates the cross section of a TSV with a bottom defect.

FIG. 1 schematically illustrates the cross section of a TSV with a defect therein. The inventors have found that such defect on the inner surface of a via, e.g. at the bottom thereof, can be effectively detected by using spectral-reflectometry measurements, where measured data characterizes interference between light reflected from the inner surface of the via and the wafer surface. This is because any defect in the via significantly alters the spectral response (as compared to a spectral signature of the same region with no via defect), e.g. alters the amplitude of a reflected signal and causes severe degradation of spectral oscillations of the signal.

Figure 2:
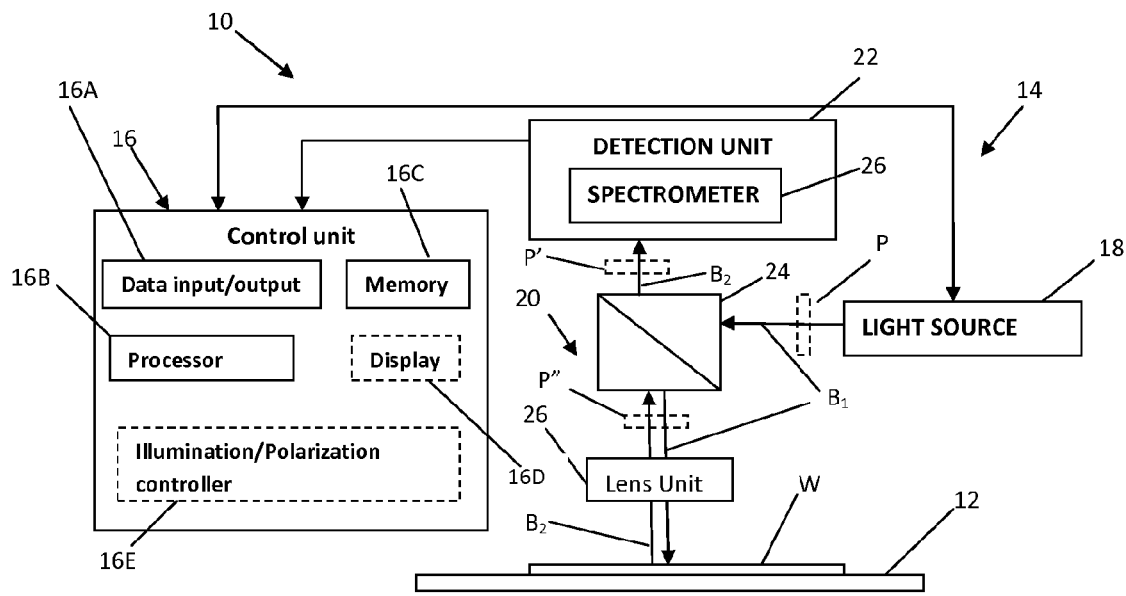
FIG. 2 is a block diagram of an inspection system of the present invention.

Reference is made to FIG. 2 showing a block diagram of a measurement system 10 used in the present invention for measuring on a wafer W (constituting a patterned structure) located on a support stage 12. The system 10 is configured and operable as a spectral-reflectometry system for measuring wavelength-dependent reflection of light from the wafer. The system 10 includes such main constructional parts as a measurement unit 14 and a control unit 16.

The measurement unit 14 may be configured for operating in one or more measurement modes, at least one being a bright field mode. In the present not limiting example, the system is illustrated for performing bright field measurements utilizing normal incidence light propagation scheme.

It should, however, be understood that the system is limited neither to normal incidence configuration nor to the use of only bright field mode. The measurement unit may be configured to monitor various via profile parameters by performing either one of or both the bight-field and the dark-field measurement modes, or a so-called "gray field" mode. The gray-field detection mode presents a predetermined combined dark and bright field detection condition for the light response signal, e.g. such as to provide a predetermined ratio between the intensity of light specularly reflected from the top surface of the structure, and the intensity of light returned from the inner surface of a via.

As shown in FIG. 2, the measurement unit 14 includes a light source unit 18, a light directing assembly 20, and a detection unit 22. The light source is a broadband source producing a light beam $B_1$ of multiple wavelengths for illuminating a region on the wafer W, and the detection 22 includes a spectrometer 26 for receiving reflections $B_2$ of the multiple wavelengths from the illuminated region. The light directing assembly 20 includes a beam splitter 24 and a lens unit 26 including for example an objective lens (that may be driven by a suitable motor for autofocusing purposes). The incident light beam $B_1$ is directed to propagate along an illumination channel impinge onto the wafer W at a certain angle (zero angle in the present example), and specularly reflected light $B_2$ propagates along a detection channel which in this example partially overlaps with the illumination channel) to the detection unit 22.

Preferably, the illuminating light is incident onto the wafer's plane with a numerical aperture (NA) not exceeding and preferably smaller than 0.1, e.g. NA=0.02 could be used.

If the use of bright- and dark-field modes, or the use of a gray field mode is considered, then an additional detection channel may be used oriented to collect light propagating outside the specular reflection path and a suitable polarization affecting assembly is provided in the illumination and dark-field detection channels; or partial masking of both the illumination and detection channels may be used. In the latter case, suitable illumination and collection masks may be selectively installable in the illumination and detection channels, thus selectively operating the system in rather bright or dark field mode, and eliminating a need for additional dark-field detection channel. Such a dark-field measurement system for measuring/monitoring various via profile parameters is described in the above indicated publication WO 2012/098550, assigned to the assignee of the present application, which is incorporated herein by reference with respect to this specific example.

The system of the invention may utilize a polarization affecting assembly including various combinations of polarizers and polarization states. As shown in a non-limiting example of FIG. 2, the polarization assembly may include one or more elements, P, P', P'', shown in the figure by dashed lines as their provision is optional. Polarizers, if used, may be accommodated in the illumination and detection channels (polarizers P and P'); or polarizers P and P' may be replaced by a common polarizer P''' accommodated in the overlapping region of the illumination and detection channels.

It should also be noted that the detection unit 22 may also include an imaging detector, and an additional beam splitter (not shown) configured as a pinhole mirror may be provided. The latter enables separation of a central part of the specularly reflected beam $B_2$ and allows its propagation towards the spectrometer 26, while reflects a periphery part of the light beam $B_2$ towards an optional imaging detector. As a result the measurement area, considered in the spectrometer 26, presents a "dark" central region, in the center of the field of view of the imaging channel. This enables to locate the measurement area in the entire illuminated region.

The output of the detection unit 22 (i.e. of the spectrometer 26 and possibly also that of an imaging detector) is coupled to the control unit 16. The control unit 16 is typically a computer system having data input/output utilities 16A, data processor and analyzer 16B, memory 16C and possibly also a display 16D. The control system may also include illumination and/or polarization and/or masking controller 16E.

As indicated above, defects in the via can be identified by analyzing spectral measured data, which corresponds to broad band light reflections from both the via surface (e.g. via bottom) and the wafer top surface. As shown more specifically in FIG. 3, a region of wafer W having via V is illuminated, and wavelength dependent reflection $B_2$ reaching the spectrometer is determined by interference properties of light portions $B_2'$ and $B_2''$ specularly reflected from respectively the via bottom $V_{surface}$ and wafer top $W_{surface}$ regions.

The control system 16 (its data input utility 16A) receives such spectral measured data, either from the measurement unit (the spectrometer 26), or generally from any storage device. The spectral measured data (raw data) is processed by the data processor and analyzer 16B, which operates to generate corresponding data indicative of a spectral response (light intensity as a function of light frequency) of the via-containing region of a wafer under measurements. Measured raw data can be processed using any known suitable software and/or hardware utility(s) e.g. using general purposes processors (control unit) or application-specific integrated circuits (ASIC) or combination thereof. Then, the processor utility 16B processes the spectral response data (light intensity-frequency function) to identify whether it is characterized by a change in one or more predetermined parameters with respect to a predetermined spectral signature of the non-defective via-containing region (e.g. includes disturbance in frequency oscillations of the light intensity). If such change is identified, the control system generates output data indicative of a possible defect in the via.

In a specific but not limiting example, the processor 16B applies Fourier transform to the intensity-frequency function and analyzes Fourier transform data to identify disturbance in frequency oscillations. Reference is made to FIGS. 4A and 4B exemplifying the spectral signature (reflectometry spectrum) for a via-containing region without a bottom defect in the via and a spectral response of the same region with a defect in the via. Preferably, regular spectrum function (intensity vs wavelength $A=f(\lambda)$ is transformed into wavenumber spectrum ($A=f'(k=2\pi/\lambda)$ because periodic oscillations are better observable in a wavenumber spectrum. The strong fast oscillations (peaks) observed in FIG. 4A correspond to interference signal from the inner surface of the via and the wafer top surface. The reflectometry signal from the via with a defect (FIG. 4B) is missing these oscillations, or at least their visibility is drastically impaired. For example, data indicative of the wavelength-dependent reflections from the via-containing region of a structure is analyzed to determine the condition of absence of one or more sharp intensity peaks (corresponding to the condition of disturbance in frequency oscillations).

Figure 5:
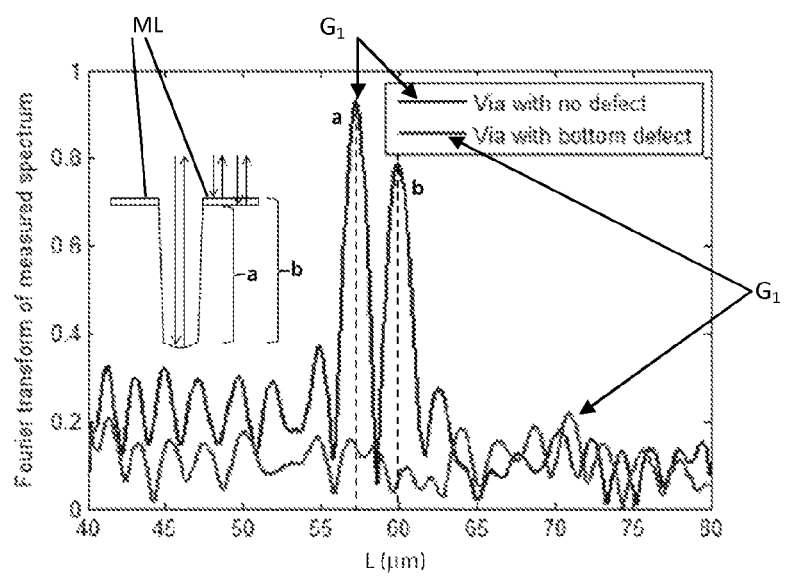
FIG. 5 graphically illustrates Fourier-transform based analysis for the data shown in FIGS. 4A and 4B.

The Fourier transform data (spectrograms) for the two examples of FIGS. 4A-4B are shown in FIG. 5 illustrating two graphs $G_1$ and $G_2$ corresponding to respectively the spectral response of the non-defected region of FIG. 4A and that of the defect-containing region of FIG. 4B. In FIG. 5, the abscissa-axis L is scaled so as to represent the deduced depth D from the oscillations frequency, through equation (1) above. For the via with no defect, two sharp peaks, marked 'a' and 'b', are observed in graph $G_1$, corresponding to depth values D≈57 μm and D≈60 μm. Such appearance of peak doubling in the Fourier spectrogram is associated with that one peak ('a') corresponds to interference between light reflected from the via bottom and the wafer surface, and a second peak, corresponding to a higher frequency in the measured signal, and accordingly to a higher measured 'depth', originates from interference between the via bottom and a hard-mask layer ML shown in the inset to FIG. 5. In marked contrast, the Fourier spectrogram for a via with a defect (graph $G_2$) shows no distinct peak, reflecting the absence of significant reflected field from the via surface.

Thus, the present invention provides a simple and effective technique for defect detection on surfaces having high aspect ratio vias. The invention can be used with any suitable spectrometry system capable of focusing illumination on a via-containing region and detection of wavelength-dependent reflection from the surface.

The invention claimed is:
1. A computer-implemented method for use in inspection of via containing structures, the method comprising:
    illuminating a via-containing region of a structure under measurement with a broadband light beam, detecting specularly reflected light, and generating measured data indicative of the detected specularly reflected light;
    receiving input data comprising data indicative of said measured data from the via-containing region;
    processing and analyzing the measured data to determine whether a possible defect exists at an inner surface of a via in said via-containing region, said processing and analyzing comprising:
        translating the measured data into data corresponding to a spectral response of the via-containing region, transforming the spectral response data into a function describing a frequency of oscillations of measured intensity in said spectral response, and, comparing said function with a spectral signature of a non-defective via-containing region, and upon identifying a disturbance in the frequency of oscillations of the measured intensity of said spectral response with respect to the spectral signature of the non-defective via-containing region, generating output data indicative of a possible defect at the inner surface of the via in said via-containing region under measurement.

2. The method of claim 1, wherein said illuminating comprises focusing said broadband light beam with normal incidence onto the via-containing region.

3. The method of claim 1, wherein said illuminating comprises focusing said broadband light beam onto the via-containing region with a numerical aperture substantially not exceeding 0.1.

4. The method of claim 1, wherein said detecting of the specularly reflected light comprises receiving said specularly reflected light by a spectrometer.

5. The method of claim 1, wherein said analyzing of the spectral response data comprises applying a Fourier transform to the spectral response data and analyzing Fourier transform data to identify the disturbance in frequency oscillations.

6. The method of claim 5, wherein said analyzing of the Fourier transform data comprises determining existence of one or more peaks.

7. The method of claim 1, wherein said illuminating and detecting comprise affecting polarization of at least one of the illuminating and specularly-reflected light beams.

8. The method of claim 1, wherein said output data is indicative of a possible defect at a bottom region of the via.

9. A system for use in inspection of via containing structures, the system comprising:
   a measurement unit configured and operable to illuminate a structure under inspection with broadband light beam, detect specularly reflected light from a via-containing region in the structure, and generate measured data indicative of the detected specularly reflected light; and
   a control system configured as a computer system being in data communication with said measurement unit, the control unit comprising:
      a data input utility configured to receive the measured data obtained from the via-containing region in the measured structure; and
      a processing and analyzing utility configured to process and analyze the measured data to determine whether a possible defect exists at an inner surface of a via in said via-containing region, by carrying out the following:
         translating the measured data into data corresponding to a spectral response of the via-containing region,
         transforming said spectral response data into a function describing a frequency of oscillations of measured intensity in the spectral response data,
         comparing said function with a spectral signature of a non-defective via-containing region, and, upon identifying a disturbance in the frequency of oscillations of the measured intensity of the spectral response with respect to the spectral signature of the non-defective via-containing region, generating output data indicative of a possible defect at the inner surface of the via in said via-containing region.

10. The system of claim 9, wherein the measurement unit comprises a broadband light source, a light directing assembly, and a detection unit comprising a spectrometer.

11. The system of claim 10, wherein the detection unit further comprises an imaging detector.

12. The system of claim 9, wherein the measurement unit is configured to operate with a normal incidence mode.

13. The system of claim 9, wherein the measurement unit is configured for illuminating the structure with numerical aperture substantially not exceeding 0.1.

14. The system of claim 9, wherein the measurement unit is configured for performing at least one of bright-field and dark-field inspection modes.

15. The system of claim 9, wherein the measurement unit is configured for performing gray-field inspection mode.

16. The system of claim 9, wherein the measurement unit comprises an illumination channel and a detection channel, and at least one polarizer located in at least one of the illumination and detection channels.

17. The system of claim 9, wherein said processing and analyzing utility is configured and operable to perform said analyzing by for applying Fourier transform to the spectral response data and analyzing Fourier transform data to identify the disturbance in frequency oscillations.

18. The system of claim 17, wherein said processing and analyzing utility is configured and operable for analyzing the Fourier transform data by determining existence of one or more peaks in the spectral response.

* * * * *